United States Patent
Uwe et al.

(10) Patent No.: US 10,610,459 B2
(45) Date of Patent: Apr. 7, 2020

(54) PROCESS FOR THE PREPARATION OF A PARTICULATE DENTAL FILLER COMPOSITION

(71) Applicant: DENTSPLY SIRONA inc., York, PA (US)

(72) Inventors: Walz Uwe, Constance (DE); Christoph Weber, Constance (DE); Maier Maximillian, Constance (DE)

(73) Assignee: DENTSPLY SIRONA Inc., York, PA (US)

( * ) Notice: Subject to any disclaimer, the term of this patent is extended or adjusted under 35 U.S.C. 154(b) by 22 days.

(21) Appl. No.: 15/548,227

(22) PCT Filed: Feb. 4, 2016

(86) PCT No.: PCT/EP2016/052357
§ 371 (c)(1),
(2) Date: Aug. 2, 2017

(87) PCT Pub. No.: WO2016/124679
PCT Pub. Date: Aug. 11, 2016

(65) Prior Publication Data
US 2018/0263862 A1 Sep. 20, 2018

(30) Foreign Application Priority Data
Feb. 5, 2015 (EP) .................................... 15154019

(51) Int. Cl.
*A61K 6/00* (2020.01)
*C09C 1/30* (2006.01)
(Continued)

(52) U.S. Cl.
CPC ............ *A61K 6/0088* (2013.01); *A61K 6/005* (2013.01); *A61K 6/0008* (2013.01);
(Continued)

(58) Field of Classification Search
CPC .................................................. A61K 6/0088
See application file for complete search history.

(56) References Cited

U.S. PATENT DOCUMENTS

| 4,503,169 A | * | 3/1985 | Randklev ............... A61K 6/083 |
| | | | 106/35 |
| 4,758,612 A | | 7/1988 | Wilson |
| (Continued) | | | |

FOREIGN PATENT DOCUMENTS

| DE | 102006046806 A1 | 12/2007 |
| WO | 02072471 A2 | 9/2002 |
| WO | 2010045105 A1 | 4/2010 |

*Primary Examiner* — Michael F Pepitone
(74) *Attorney, Agent, or Firm* — Dentsply Sirona Inc.

(57) ABSTRACT

Process for the preparation of a particulate dental filler composition, comprising the following steps: (a) introducing a mixture containing (a1) a silica precursor component, and (a2) a solution or dispersion of one or more compounds selected from compounds of aluminum, zinc, titanium, zirconium, tungsten, ytterbium, hafnium, bismuth, barium, strontium, silver, tantalum, lanthanum, tin, boron, and cerium, into a pulsed reactor; (b) converting the silica precursor component and the compounds into a particulate mixed oxide with a pulsed gas flow resulting from flameless combustion; (c) isolating the particulate mixed oxide from the pulsed reactor; (d) optionally subjecting the particulate mixed oxide to a heat treatment step; and (e) treating the optionally heat-treated particulate mixed oxide with a silane treatment agent for obtaining a particulate dental filler composition.

5 Claims, 1 Drawing Sheet

(51) Int. Cl.
  *A61K 6/083*  (2006.01)
  *A61K 6/02*  (2006.01)
  *C01B 13/20*  (2006.01)
  *A61K 6/08*  (2006.01)
  *C01B 33/20*  (2006.01)

(52) U.S. Cl.
  CPC .......... *A61K 6/0038* (2013.01); *A61K 6/0073* (2013.01); *A61K 6/024* (2013.01); *A61K 6/025* (2013.01); *A61K 6/0205* (2013.01); *A61K 6/0235* (2013.01); *A61K 6/0245* (2013.01); *A61K 6/0255* (2013.01); *A61K 6/08* (2013.01); *A61K 6/083* (2013.01); *C01B 13/20* (2013.01); *C01B 33/20* (2013.01); *C09C 1/30* (2013.01); *C09C 1/3081* (2013.01); *C01P 2006/12* (2013.01)

(56) References Cited

U.S. PATENT DOCUMENTS

| | | | |
|---|---|---|---|
| 4,814,362 A | 3/1989 | Billington | |
| 5,079,277 A | 1/1992 | Wilson | |
| 5,338,773 A | 8/1994 | Lu | |
| 5,710,194 A | 1/1998 | Hammesfahr | |
| 7,358,212 B2 * | 4/2008 | Remke | B01J 6/001 502/302 |
| 8,658,188 B2 | 2/2014 | Stark | |
| 2012/0121804 A1 | 5/2012 | Sekino | |
| 2013/0158157 A1 | 6/2013 | Stelzig | |
| 2014/0039088 A1 * | 2/2014 | Stelzig | A61K 6/0023 523/116 |
| 2018/0263862 A1 * | 9/2018 | Uwe | A61K 6/0038 |

* cited by examiner

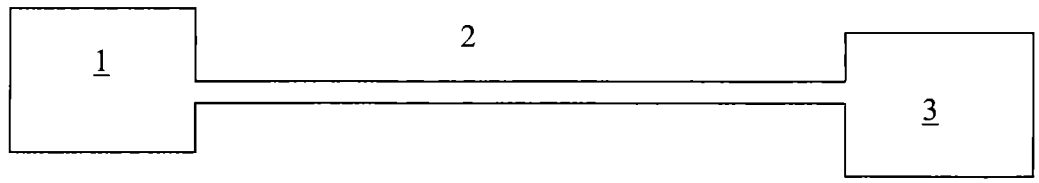

PROCESS FOR THE PREPARATION OF A PARTICULATE DENTAL FILLER COMPOSITION

CROSS-REFERENCE TO RELATED APPLICATION

This application is a national stage application of PCT/EP2016/052357, filed Feb. 4, 2016, which claims priority to European Patent Application No. 15154019.2, filed Feb. 5, 2015.

FIELD OF THE INVENTION

The present invention relates to a process for the preparation of a particulate dental filler composition. Moreover, the present invention relates to a particulate dental filler composition obtainable by the process of the present invention. Furthermore, the present invention relates to the use of the dental filler composition of the invention in a dental composition. The present invention also relates to a dental restorative material containing the particulate dental filler composition obtainable by the process of the present invention. Finally, the present invention relates to a process for the preparation of a dental restorative material comprising a step of incorporating the dental filler composition into a dental resin matrix.

The process of the present invention provides mixed oxide precursor particles comprising silicon and one or more additional metals, metalloids and/or lanthanoids in a controlled and efficient manner in a single step. The mixed oxide precursor particles may comprise a coating prepared in the same step by applying a coating on initially formed mixed oxide particles. The precursor particles are silanated for obtaining a particulate dental filler composition of the present invention. The particles have a spherical particle shape, a small particle size and narrow particle size distribution, excellent particle morphology and suitable surface properties. Milling of the mixed oxide precursor particles is not necessary according to the present invention since agglomerates are avoided.

A dental restorative material containing the particulate dental filler composition of the present invention has excellent mechanical properties and shows good polishability, wear-resistance, gloss, gloss retention and opalescence.

BACKGROUND OF THE INVENTION

Curable dental restorative materials containing a particulate filler are known. Generic dental restorative materials have to meet a number of requirements. First and foremost, the toxicity of a dental restorative material must be low to be suitable for use in the oral environment. Moreover, mechanical properties such as strength and abrasion resistance must be high in a cured dental material for applications where mastication forces represent the primary challenge to the performance of the dental restorative material. Good aesthetic properties such as luster and translucency are required in applications where the location of a dental restoration is visible.

The presence of a particulate filler in a dental restorative material increases the mechanical strength and improves the surface properties of the cured dental material. Specifically, a particulate filler having a median particle size (D50) in the range of 0.05 to 5 μm provides good surface properties and mechanical properties. However, in case the particulate dental filler contains particles having a diameter in the range of the wavelength of visible light (400 to 800 nm), the luster and aesthetic character of the dental restorative material deteriorate the more the refractive index of the filler deviates from the refractive index of the cured resin matrix.

In dental restorative materials such as dental composites containing a curable resin, resin shrinkage upon polymerization in the curing process tends to cause gap formation between the restorative composite and the tooth. As a consequence micro leakage, secondary caries and decreased longevity of the restoration represents a problem with prior dental restorative materials. In order to alleviate the shrinking problem and to reinforce dental restorative materials, a high filler load is preferred.

Accordingly, spherical composite particles containing inorganic particles in an organic matrix were suggested previously in order to improve the aesthetic properties while maintaining good mechanical properties and while avoiding the shrinking problem.

EP2604247 discloses a process for the preparation of composite filler particles, comprising: coating a particulate filler having a median particle size (D50) of from 1 to 1200 nm with a coating composition containing a film-forming agent, agglomerating the coated particulate filler, whereby the agglomeration is carried out by spray agglomeration or growth agglomeration, and crosslinking the granulation of the coated particulate filler for providing composite filler particles having a median particle size (D50) of from 1 to 70 μm, wherein the particulate filler is the main component by volume of the composite filler particles.

On the other hand, filler particles prepared in a conventional sol-gel method are known. According to the sol-gel method, spherical silica particles of high mono-dispersion and small average particle size may be produced by subjecting an alkoxide of silicon to hydrolysis and polycondensation. By using an alkoxide of silicon and an alkoxide of a metal other than silicon as raw materials, silica-based composite oxide particles can be produced by the sol-gel processing. Previously, particles of silica-titania, silica-alumina, or silica-zirconia were disclosed as the silica-based composite oxide particles. The silica-based composite oxide particles produced by the sol-gel processing are provided with characteristic properties depending upon the kind of the metal oxide contained in the particles together with silica. For example, by changing the mixing ratio of silica and a metal oxide other than silica, the refractive index of the particles may be adjusted while the optical transparency of the particles is maintained. Accordingly, a transparent composite resin or a dental composite resin may be obtained wherein the refractive index of the particles is similar to the refractive index of the polymerizable matrix.

Moreover, it is necessary that the particulate dental filler composition has radioopacity in addition to the transparency. Accordingly, by controlling the mixing ratio of a metal oxide to make the refractive index of filler identical with that of the cured resin, there can be obtained a dental filler having both transparency and radioopacity.

However, silica-based composite oxide particles formed by sol-gel processing tend to coagulate and to form aggregates of primary particles. Moreover, the diameters of the particles formed become non-uniform over time.

WO2010/045105 discloses fillers containing silica-zirconia nanoclusters. The fillers are prepared by mixing a sol of silica nanoparticles with a sol of preformed, crystalline nanozirconia particles. Subsequently, the mixture is heated to a temperature from about 400° C. to about 1000° C.

According to WO2010/045105, the milling of the heated mixture is essential to form a filler comprising silica-zirconia nanoclusters.

EP2463235 discloses a method for producing silica-zirconia composite oxide particles each coated with a silica layer. Accordingly, a liquid dispersion of silica-zirconia composite oxide particles is obtained by reacting an alkoxide of silicon with an alkoxide of zirconium in a water-containing solvent that contains acetonitrile so that the reaction liquid is to contain not less than 10% by mass of acetonitrile. Subsequently, the surface of each silica-zirconia composite oxide particle is coated with a silica layer by reacting the silica-zirconia composite oxide particles dispersed in the liquid dispersion with an alkoxide of silicon and/or a condensable compound derived from the alkoxide in the liquid dispersion of silica-zirconia composite oxide particles. The presence of a substantial amount of acetonitrile is essential for preventing the particles from coagulating.

Therefore, it is difficult to provide silica-based composite oxide particles of high mono-dispersion and uniform particle diameter by the sol-gel method so that a high filler load in a dental composition is difficult to attain.

U.S. Pat. No. 8,658,188 discloses a nanoparticulate bioactive radio-opaque material for use in dental compositions, which comprises a matrix containing oxides of Si, Ca, Na and optionally P. A radiopacifier embedded in the matrix is selected from the group consisting of metals, metal oxides and metal salts (such as phosphates, halogenides, sulphates) of elements with an atomic mass greater than 20, preferably greater than 85. The particles are prepared by flame pyrolysis at a high flame temperature of up to 2600° C. and are obtained as aggregates having a large BET surface of at least 30 m$^2$/g. Due to the low bulk density and snow-like behavior, compaction of the particles is necessary prior to incorporation into a dental composition. However, the aggregates of nanoparticles increase the viscosity of a dental composition to an extent which is not useful in practice.

U.S. Pat. No. 4,503,169 discloses radiopaque, low visual opacity dental composites and non-vitreous microparticles for use therein, the microparticles individually containing amorphous silica microregions interspersed with radiopacifying polycrystalline ceramic metal oxide microregions. U.S. Pat. No. 6,030,606 discloses dental restoratives.

DISCLOSURE OF THE INVENTION

It is a problem of the present invention to provide a process for the efficient preparation of a particulate dental filler which affords excellent mechanical properties, as well as good polishability, wear-resistance, gloss, gloss retention and opalescence after curing of a dental restorative material containing the particulate dental filler while maintaining appropriate viscosity for good workability of the dental restorative material, and lower shrinkage during polymerization.

According to a first aspect, the present invention provides a process for the preparation of a particulate dental filler composition, comprising the following steps:
(a) introducing a mixture containing
  (a1) a silica precursor component, and
  (a2) a solution or dispersion of one or more compounds selected from compounds of aluminum, zinc, titanium, zirconium, tungsten, ytterbium, hafnium, bismuth, barium, strontium, silver, tantalum, lanthanum, tin, boron, and cerium,
  into a pulsed reactor;
(b) converting silica precursor component and the compounds into a particulate mixed oxide with a pulsed gas flow resulting from flameless combustion;
(c) isolating the particulate mixed oxide from the pulsed reactor;
(d) optionally subjecting the particulate mixed oxide to a heat treatment step; and
(e) treating the optionally heat-treated particulate mixed oxide with a silane treatment agent for obtaining a particulate dental filler composition.

According to a second aspect, the present invention provides a dental filler composition obtainable according to the process according to the first aspect.

According to a third aspect, the present invention provides a use of the dental filler composition according to the second aspect in a dental composition.

According to a fourth aspect, the present invention provides a dental restorative material comprising
(i) the dental filler composition as defined by the second aspect;
(ii) one or more polymerizable compounds and/or one or more polymers; and optionally
(iii) a polymerization initiator system.

According to a fifth aspect, the present invention provides a process for the preparation of a dental restorative material as defined by the fourth aspect, comprising a step of incorporating the dental filler composition into a dental resin matrix.

The present invention is based on the recognition that a superior particulate dental filler composition may be obtained by using a pulsed reactor followed by a silanation of the surface of the particles. The formation of the unsilanated particular dental filler composition may be carried out in a single step in the pulsed reactor, whereby silanation may subsequently be carried out without the need of a prior milling step. The single step reaction in the pulsed reactor may include the formation of an additional coating of the surface of the particulate dental filler during the treatment in the pulsed reactor. According to the process of the invention, atomization of the starting materials, drying of the precursor compounds, particle formation by polycondensation and calcination reactions, and optionally coating may be carried out in a single step.

According to the process of the present invention, a mixture containing a silica precursor component, and a solution or dispersion of one or more specific compounds is introduced into a pulsed reactor and is converted into a mixed oxide comprising a plurality of elements. The resultant finely divided mixed oxide powder comprising a plurality of elements is characterized by a combination of spherical particle shape, dense and amorphous particle morphology, high surface activity for silanation, and narrow particle size distribution, and optionally the presence of an additional coating, which finely divided mixed oxide powder is advantageous for use in the production a dental restorative material after silanation of the particle surface.

BRIEF DESCRIPTION OF THE DRAWINGS

FIG. 1 shows a pulsed reactor used in the process of the present disclosure.

DETAILED DESCRIPTION OF THE PREFERRED EMBODIMENTS

The present invention provides a process for the preparation of a particulate dental filler composition. The particulate dental filler composition comprises a plurality of mixed oxide particles optionally containing carbides, nitrides, silicides and borides, said particles having a silanated outer surface. The particles are preferably spherical. The particles are preferably essentially non-agglomerated. The particles are preferably dense. The particles preferably have a narrow particle size distribution and a nanoscale median particle size.

The particulate dental filler composition are particularly useful for the preparation of a dental composition. A dental composition is preferably a dental restorative material. The dental restorative material may be selected from a dental composite, a dental cement or a resin reinforced dental cement. A dental composite may be a highly filled dental composite, a flowable composite, a compomer, a root canal sealer, or a pit and fissure sealant. A dental cement may be a glass ionomer cement or a luting cement.

The process for the preparation of a particulate dental filler composition of the present invention comprises a step of introducing a mixture containing a silica precursor component, and a solution or dispersion of one or more compounds selected from compounds of aluminum, zinc, titanium, zirconium, tungsten, ytterbium, hafnium, bismuth, barium, strontium, silver, tantalum, lanthanum, tin, boron, and cerium, into a pulsed reactor.

The pulsed reactor facilitates a thermal process for manufacturing the fine particulate filler. In contrast to spray drying, thermal decomposition and oxidation of the starting materials take place in addition to evaporation or burning of the solvent in the process of the present invention.

A pulsed reactor consists of a combustion chamber, a resonance tube and a cyclone or filter for powder separation. A suitable pulsed reactor is known from WO 02/072471 or DE 10 2004 044 266. A pulsed reactor used in the process of the present invention is shown in FIG. 1. The reactor includes a combustion chamber 1, to which a resonance tube 2 having a significantly reduced flow cross section compared with the combustion chamber is connected on the exhaust-gas side. The combustion chamber base is fitted with one or more valves for the entry of the combustion gases. The valves are fluidically and acoustically matched to the combustion chamber and the resonance-tube geometry such that the pressure waves, created in the combustion chamber, of the homogeneous flameless temperature field spread pulsating predominantly in the resonance tube. Thus a so-called Helmholz resonator with pulsating flow forms. Pulsation can be regular or irregular. Material is typically fed into the reaction chamber either with an injector or with a suitable two-component nozzle and a Schenk dispenser. The particulate filler is separated from the gas flow using a suitable filter 3.

The pulsed reactor is used to thermally treat gas-borne matter. Accordingly, a pulsating flow of hot gas is generated within the combustion chamber of the reactor by burning a fuel gas such as a hydrocarbon gas or hydrogen, with air. The fuel gas may be any gas which is suitable for the production of hot gas. Natural gas and/or hydrogen mixed with air or, if desired, oxygen are preferred. However, propane or butane, may also be used.

Hot gas can be generated in two different ways. Either the hot gas generator works with a high level of excess air or the hot gas atmosphere can be generated with little oxygen or none at all. The hot gas temperatures in the pulsed reactor range from 250° to 1,400° C. However, the actual treatment temperature may differ significantly from these values after the reactant has been added.

The combustion chamber is provided with valves which control the gas supply into the combustion chamber. The process of valve closing and opening occurs self-regulated due to pressure changes within the combustion chamber as follows.

The combustion-gas mixture entering the combustion chamber is ignited and combustion produces a pressure wave towards the resonance tube. The out-flow of gas produces a vacuum in the combustion chamber so that a fresh gas mixture flows into the combustion chamber and ignites, thereby repeating the cycle. The pulsed combustion process in the combustion chamber initiates an acoustic vibration in the resonance tube which has a high degree of turbulence. Moreover, a flow with an almost constant temperature across the pipe diameter is generated in the resonance tube wherein the formation of the particulate dental filler takes place, through the pulsating flow of hot gas. The tube-shaped flow results in a narrow residence time distribution. Furthermore, the pulsating hot gas flow results in an increased convective heat and mass transfer to and/or from the particles. Therefore, the mixture of starting materials is subject to the same thermal treatment anywhere in the reaction space. Accordingly, local overheating and wall deposits, which would result in the formation of coarse and hard agglomerates are avoided.

The reaction parameters and reaction medium of the pulsed reactor are adjusted in order to provide the properties of the particulate mixed oxide in terms of particle shape, particle size, particle morphology, and surface properties.

The pulsation frequency can be set via the reactor geometry and varied via the temperature. The gas flow resulting from flameless combustion preferably pulses at from 10 to 150 Hz, particularly preferably at from 20 to 100 Hz.

The degree of aggregation and the size of the primary particles may be adjusted by adjusting the maximum process temperature and the residence time. Aggregates are formed in thermal processes wherein sintering takes place, whereby sintering entails a partial fusion of the particle material. The process temperature required for sintering depends on the initial particle size. In general, the smaller the particle size, the lower the required process temperature for sintering. When sintering occurs, the particles grow. When the proportion of the fused material increases, particles form stable aggregates upon cooling after the thermal process. Accordingly, it is desirable to adjust the process temperature to a low level so that formation of aggregates is avoided. Preferably, the process temperature is adjusted to a level of less than 1000° C. more preferably less than 900° C. If the process temperature is too low, then the formation of mixed oxide particles is incomplete. Therefore, it is preferred to adjust the process temperature to a level of at least 400° C., more preferably at least 500° C. Advantages of the process according to the invention are that, for example, suspensions can usually be calcined within a very short period of time, typically within a few milliseconds, at comparatively low temperatures without additional filtration and/or drying steps or without the addition of additional solvents. The possibility of already very precisely determining the stoichiometry when choosing the starting materials is a further advantage of the process according to the invention.

With respect to the combustion-chamber pressure and the gas velocity in the resonance tube, non-steady-state conditions exist, ensuring very fast and extensive energy transfer from the pulsed hot gas flow to the solid particles. High reaction rates are achieved at very short residence times in the millisecond range. Accordingly, a high yield of defined mixed oxide particles can be prepared.

In the process according to the present invention, the combustion air also serves as carrier gas for material transport in the reactor.

According to the invention, the mixture containing a silica precursor component, and a solution or dispersion of one or more compounds selected from compounds of aluminum, zinc, titanium, zirconium, tungsten, ytterbium, hafnium, bismuth, barium, strontium, silver, tantalum, lanthanum, tin, boron, and cerium can be introduced either directly into the combustion chamber of the pulsed reactor or into the resonance tube of the pulsed reactor, which is connected to the combustion chamber. The introduction into the resonance tube has the advantage that the combustion process is separated from the chemical reactions forming the mixed oxide particles. Accordingly, the silica and the compounds are converted into a particulate mixed oxide with a pulsed gas flow resulting from flameless combustion.

Besides the variation of process parameters in the pulsed reactor, the resultant particle size can also be influenced by specifically influencing the starting suspension or dispersion.

The mixture contains a silica precursor component. The silica precursor component is a compound or particle which forms silica structures in a pulsed gas flow resulting from flameless combustion when contained in the mixture in the absence of the solution or dispersion of the one or more compounds. In the presence of the solution or dispersion of the one or more compounds, the silica precursor component may form silica structures or mixed oxide structures. The formation of silica structures based on the silica precursor component is based on condensation of silanol groups and/or oxidation of a silicon containing compound.

The silica precursor component may be a silica colloidal dispersion which may comprise an alkoxide represented by the general formula (I) or (II):

$$Si(OR)_4 \quad (I)$$

$$SiR'_n(OR)_{4-n} \quad (II)$$

wherein R and R', which may be the same or different, are each a hydrocarbon group which may contain an ether bond or an ester bond, and n is an integer of 1 to 3. As the hydrocarbon groups of R and R', an alkyl group is preferred. Preferably, R and R' are $C_{1-6}$ alkyl group such as methyl group, ethyl group, isopropyl group, butyl group or the like. A particularly preferred silica precursor component is tetraethyl orthosilicate (TEOS) with the formula $Si(OC_2H_5)_4$.

Alternatively or additionally, the silica colloidal dispersion may comprise a condensation product obtained by partial hydrolysis of the alkoxide represented by the general formula (I) or (II).

The silica precursor component may be a composition containing silicic acid or a condensation product thereof having the general formula $[SiO_x(OH)_{4-2x}]_n$ wherein x and n are integers.

The silica precursor component may be a solution or dispersion of an alkali metal silicate. Examples of the alkali metal silicate are sodium silicate and potassium silicate. Sodium silicate is the common name for compounds with the formula $Na_2(SiO_2)_nO$, wherein n is an integer, such as sodium metasilicate, $Na_2SiO_3$.

The silica precursor component may be an organosilicon compound containing carbon-silicon bonds such as hexamethyldisiloxane.

The silica precursor component may be used in pure form or as a solution or dispersion of the silica precursor in a suitable solvent or dispersant.

The mixture further contains one or more compounds selected from compounds of aluminum, zinc, titanium, zirconium, tungsten, ytterbium, hafnium, bismuth, barium, strontium, silver, tantalum, lanthanum, tin, boron, and cerium. Aluminum, zinc, titanium, zirconium, tungsten, ytterbium, hafnium, bismuth, barium, and strontium are preferred. Zirconium, tungsten, ytterbium, bismuth, barium, and strontium are more preferred. According to a preferred embodiment, the mixture further contains one or more compounds of zirconium. According to a further preferred embodiment, the mixture further contains one or more compounds of zirconium and tungsten. According to a further preferred embodiment, the mixture further contains one or more compounds of zirconium and ytterbium. According to a further preferred embodiment, the mixture further contains one or more compounds of zirconium and bismuth.

The compounds are introduced in the form of an aqueous salt solution or suspension of nitrates, carboxylates such as acetates, oxalates, citrates, lactates, and tartrates, halogenides such as chlorides and fluorides, hydroxides, carbonates, alkoxides, phosphates and/or of the corresponding metals. Moreover, metals may be chelated by suitable chelating ligands such as EDTA. In a preferred embodiment of the process according to the invention, citric acid or a citric acid salt or maleic acid or its derivatives is additionally introduced into the mixture of the starting compounds.

Alternatively, an alkoxide or a salt of aluminum, zinc, titanium, zirconium, tungsten, ytterbium, hafnium, bismuth, barium, strontium, silver, tantalum, lanthanum, tin, boron, and cerium may be used. Specifically, an alkoxide obtained by replacing the Si in the above-mentioned general formula (I) or (II) of the alkoxide of silicon, with one or more atoms selected from compounds of aluminum, zinc, titanium, zirconium, tungsten, ytterbium, hafnium, bismuth, barium, strontium, silver, tantalum, lanthanum, tin, boron, and cerium; a condensation product obtained by partial hydrolysis of the alkoxide of one or more compounds selected from compounds of aluminum, zinc, titanium, zirconium, tungsten, ytterbium, hafnium, bismuth, barium, strontium, silver, tantalum, lanthanum, tin, boron, and cerium, or a mixture thereof, may be mentioned. An alkoxide or a salt of zirconium, tungsten, ytterbium, bismuth, barium, and strontium are more preferred. According to a preferred embodiment, the mixture further contains one or more alkoxides of zirconium. According to a further preferred embodiment, the mixture further contains one or more alkoxides or salts of zirconium and tungsten. According to a further preferred embodiment, the mixture further contains one or more alkoxides or salts of zirconium and ytterbium. According to a further preferred embodiment, the mixture further contains one or more alkoxides or salts of zirconium and bismuth. A particularly preferred compound is tetra-n-propyl zirconate.

The content of boron and/or the one or more metals, determined as oxides, is selected appropriately depending upon the application purpose of the particles. When the particles are used as a filler for a dental composite resin, the content of the one or more heavy metals is determined in view of the transparency and radioopacity. The content of the one or more heavy metals is generally preferably 5 to 50 mol %, more preferably 10 to 30 mol %.

The mixture may further contain a solvent or dispersant. Suitable solvents and dispersants may be selected from water and organic solvents. Organic solvents may be selected from an organic inert solvent or solvent mixture (usually hydrocarbon based), for example, undecane, dodecane or corresponding commercially available mineral oil mixtures or more volatile hydrocarbons, for example, hexane, heptane, octane, decane, toluene, ethylbenzene or cumene. In particular, the organic solvent may be aliphatic hydrocarbon solvents such as n-pentane, i-pentane, n-hexane, i-hexane, n-heptane, i-heptane, 2,2,4-trimethyl-pentane, n-octane, i-octane, cyclohexane, and methylcyclohexane; aromatic hydrocarbon solvents such as benzene, toluene, xylene, ethylbenzene, trimethylbenzene, methylethylbenzene, n-propylbenzene, i-propylbenzene, diethylbenzene, i-butylbenzene, triethylbenzene, di-i-propylbenzene, n-amylnaphthalene, and trimethylbenzene; monoalcohol solvents such as methanol, ethanol, n-propanol, i-propanol, n-butanol, i-butanol, sec-butanol, t-butanol, n-pentanol, i-pentanol, 2-methyl-butanol, sec-pentanol, t-pentanol, 3-methoxybutanol, n-hexanol, 2-methylpentanol, sec-hexanol, 2-ethylbutanol, sec-heptanol, heptanol-3, n-octanol, 2-ethylhexanol, sec-octanol, n-nonyl alcohol, 2,6-dimethylheptanol-4, n-decanol, sec-undecyl alcohol, trimethylnonyl alcohol, sec-tetradecyl alcohol, sec-heptadecyl alcohol, phenol, cyclohexanol, methylcyclohexanol, 3,3,5-trimethylcyclohexanol, benzyl alcohol, phenyl methyl carbinol, diacetone alcohol, and cresol; polyalcohol solvents such as ethylene glycol, propylene glycol, 1,3-butylene glycol, pentanediol-2,4,2-methylpentanediol-2,4, hexanediol-2,5, heptanediol-2,4,2-ethylhexanediol-1,3, diethylene glycol, dipropylene glycol, triethylene glycol, tripropylene glycol, and glycerin; ketone solvents such as acetone, methylethyl ketone, methyl-n-propyl ketone, methyl-n-butyl ketone, diethyl ketone, methyl-i-butyl ketone, methyl-n-pentyl ketone, ethyl-n-butyl ketone, methyl-n-hexyl ketone, di-i-butyl ketone, trimethylnonanone, cyclohexanone, methylcyclohexanone, 2,4-pentanedione, acetonylacetone, diacetone alcohol, acetophenone, and fenchone; ether solvents such as ethyl ether, i-propyl ether, n-butyl ether, n-hexyl ether, 2-ethylhexyl ether, ethylene oxide, 1,2-propylene oxide, dioxolane, 4-methyl-dioxolane, dioxane, dimethyl dioxane, ethylene glycol monomethyl ether, ethylene glycol monoethyl ether, ethylene glycol diethyl ether, ethylene glycol mono-n-butyl ether, ethylene glycol mono-n-hexyl ether, ethylene glycol monophenyl ether, ethylene glycol mono-2-ethylbutyl ether, ethylene glycol dibutyl ether, diethylene glycol monomethyl ether, diethylene glycol monoethyl ether, diethylene glycol diethyl ether, diethylene glycol mono-n-butyl ether, diethylene glycol di-n-butyl ether, diethylene glycol mono-n-hexyl ether, ethoxy triglycol, tetraethylene glycol di-n-butyl ether, propylene glycol monomethyl ether, propylene glycol monoethyl ether, propylene glycol monopropyl ether, propylene glycol monobutyl ether, dipropylene glycol monomethyl ether, dipropylene glycol monoethyl ether, dipropylene glycol monopropyl ether, dipropylene glycol monobutyl ether, tripropylene glycol monomethyl ether, tetrahydrofuran, and 2-methyltetrahydrofuran; ester solvents such as diethyl carbonate, methyl acetate, ethyl acetate, γ-butyrolactone, γ-valerolactone, n-propyl acetate, i-propyl acetate, n-butyl acetate, i-butyl acetate, sec-butyl acetate, n-pentyl acetate, sec-pentyl acetate, 3-methxoybutyl acetate, methylpentyl acetate, 2-ethylbutyl acetate, 2-ethylhexyl acetate, benzyl acetate, cyclohexyl acetate, methylcyclohexyl acetate, n-nonyl acetate, methyl acetoacetate, ethyl acetoacetate, ethylene glycol monomethyl ether acetate, ethylene glycol monoethyl ether acetate, diethylene glycol monomethyl ether acetate, diethylene glycol monoethyl ether acetate, diethylene glycol mono-n-butyl ether acetate, propylene glycol monomethyl ether acetate, propylene glycol monoethyl ether acetate, propylene glycol monopropyl ether acetate, propylene glycol monobutyl ether acetate, dipropylene glycol monomethyl ether acetate, dipropylene glycol monoethyl ether acetate, glycol diacetate, methoxy triglycol acetate, ethyl propionate, n-butyl propionate, i-amyl propionate, diethyl oxalate, di-n-butyl oxalate, methyl lactate, ethyl lactate, n-butyl lactate, n-amyl lactate, diethyl malonate, dimethyl phthalate, and diethyl phthalate; nitrogen-containing solvents such as N-methylformamide, N,N-dimethylformamide, N,N-diethylformamide, acetamide, N-methylacetamide, N,N-dimethylacetamide, N-methyl-propionamide, and N-methylpyrrolidone; and sulfur-containing solvents such as dimethyl sulfide, diethyl sulfide, thiophene, tetrahydrothiophene, dimethyl sulfoxide, sulfolane, and 1,3-propanesulfone. These solvents may be used singly or in combination of two or more.

The mixed oxide particles produced according to the present invention may not necessarily be constituted by silica and the specific additional elements only. The particles may contain an amount of other metal oxide, metalloid oxide and/or lanthanoid oxide as long as the desired properties of metal oxide particles are maintained or improved. Generally, the content of the metal oxide, metalloid oxide and/or lanthanoid oxide other than the essential metal oxide, metalloid oxide and/or lanthanoid oxide is preferably 50 percent by weight or less, more preferably 30 percent by weight or less. According to a specific embodiment, the content of the oxides other than the essential oxides is preferably 5 percent by weight or less.

In case a bioactive particulate dental filler composition is prepared, which is adapted to induce calcium phosphate deposition on the surface of the particulate in a fluid in a living organism, the particulate dental filler composition preferably contains calcium and sodium.

Precursors for the metal oxides, metalloid oxides and/or lanthanoid oxides other than the essential metal oxides, metalloid oxides and/or lanthanoid oxides may be incorporated into the mixture. Specific examples of the precursors are sodium 2-ethylhexanoate or any kind of soluble sodium source such as sodium carboxylate, calcium 2-ethylhexanoate or any kind of soluble calcium source such as calcium carboxylate.

The mixture may further contain a surfactant. Suitable surfactants include Polysorbat 20 (Tween 20®), Polysorbat 80 (Tween 80), Pullulan, and Sodium dodecyl sulphate (SDS). The surfactant may be present in an amount of from 0.1 to 10 percent by weight based on the entire weight of the mixture.

The mixture provides an essentially homogeneous composition of the mixed oxide particles. According to the present invention, particles having domains with oxides of different composition are not preferred.

Preferably, the mixture contains a solvent. The solvent is preferably water. However, one or more volatile organic solvents may also be used either alone or in combination.

The formation of finer particles with a more uniform spherical shape may be facilitated by the addition of one or more surfactants and/or emulsifiers. Accordingly, a fatty alcohol ethoxylate may be added in an amount of 1 to 10% by weight, preferably 2 to 8% by weight, based on the total amount of the suspension or dispersion.

Moreover, the particle size distribution may be adjusted to be narrow by a one- or multistage wet-chemical intermediate step before the thermal treatment in the pulsed reactor. For this purpose, the particle size can firstly be adjusted in the starting mixture, for example, via coprecipitation.

The mixture can be introduced into the reactor either in the form of a solution, suspension or dispersion. Solutions, suspensions or dispersions are preferably introduced in extremely finely divided form by means of one or more nozzles. Typically, the mixture from which the mixed metal oxide powders according to the invention are prepared is introduced into the combustion chamber, directly via a carrier fluid, in particular a carrier gas, preferably an inert carrier gas, such as for example nitrogen. Rapid water or organic solvent removal or thermal decomposition of the reactants instantaneously occurs, and the intermediate solid particles can react in the hot gas flow reaction through thermal conversion and oxidation to form the mixed oxide.

The gas flow resulting from the pulsed combustion in the pulsed reactor has flow turbulences whose degree of turbulence is preferably from 5 to 10 times greater than the degree of turbulence of steady-state flow. The temperature of the gas flow in the combustion chamber of the pulsed reactor is preferably above 250° C., in particular above 1400° C.

The properties of the particulate mixed oxide starting out from a given mixture, may be adjusted by adjusting the introduction of the mixture, the treatment temperature, the type of hot gas atmosphere, as well as the frequency and amplitude of the pulsation. For example, a variation of the nozzle diameter and/or the compressed air fed to the nozzle enables the droplet size during feeding into the pulsed reactor to be influenced. The same applies to the targeted control of the temperature profile and/or variation of the residence time.

The reactants are treated by the hot gas flowing through the resonance tube. After the treatment, the reaction gas is cooled. After the formation of the particulate mixed oxide, the particles produced in the reactor are isolated from the pulsed reactor. Accordingly, the particles are separated from the gas flow in a suitable separator. A separator may be selected from a gas cyclone, a surface filter or an electrostatic filter. The reaction gas is cooled to the temperature necessary depending on the filter type before entering the separator. Accordingly, a heat exchanger may be provided and/or by cooling gases may be introduced into the exhaust-gas flow. By varying the oxygen partial pressure during introduction of the cooling gases, the phase composition of the powder can be influenced.

The particulate mixed oxide may optionally be subjected to a heat treatment step depending on the powder type, desired phase composition and application. In a specific embodiment, the particulate mixed oxide can be subjected to heat treatment at a temperature in the range from 500 to 950° C., preferably from 550 to 800° C. The heat treatment may be carried out in a powder bed in a chamber, tubular, tunnel, belt or rotary tube furnace or in a fluidised bed. If necessary, the particulate dental filler is subjected to grinding by means of an air-jet mill, grinding-media mill, impact mill or other milling machines.

According to a specific embodiment, the particulate dental filler may be subject to in situ coating in the pulsed reactor as disclosed in DE102006046806. The coating may be a partial coating. The coating may be used for adjusting the refractive index, for improving abrasion resistance or for rendering the surface of the particles inert or controlling the release of, for example, fluoride from the particles or the coating. The coating may be an oxide coating and/or the coating may be a carbide coating, a nitride coating, a silicide coating a fluoride coating or a mixture thereof.

An oxide coating may contain silica, aluminum oxide, or titanium oxide. A carbide coating may contain silicon carbide. A nitride coating may contain boron nitride, silicon nitride, or aluminum nitride. A silicide coating may contain tungsten silicide, titanium disilicide, or magnesium silicide. An oxide coating such as a metal oxide coating, a metalloid coating and/or a lanthanoid coating may be used to adapt the optical properties and the surface properties of the filler particles. A carbide, a nitride coating, a silicide coating or a mixture thereof may be useful for improving the abrasion resistance of the filler particles.

The coating is prepared based on a coating mixture. The coating mixture may contain precursor compounds such as nitrate, phosphates, carbonates, hydrogencarbonates, carboxylates, alcoholates, acetate, oxalate, citrate, halogenides, sulfate, organometal compounds, and hydroxide.

The coating mixture may further comprise a solvents and dispersant. Suitable solvents may be selected from water or organic solvents. Organic solvents may be selected form methanol, ethanol, DMSO, acetonitrile and the like. Dispersants may be non-surface active polymers or surface-active substances which improve the separation of particles and prevent settling or clumping.

The process may be controlled, for example, with regard to the temperature at the point of addition of the coating mixture, the residence time, and/or the choice of the starting material so that the desired coating may be provided.

The mixture may be introduced into the reactor in a finely divided form of the solution, suspension of dispersion as disclosed in DE102006046806.

Subsequently, the particulate mixed oxide or the heat-treated particulate mixed oxide are treated with a silane treatment agent for obtaining a particulate dental filler composition of the present invention. Accordingly, the surface of the particulate mixed oxide is modified by a silane treatment agent. Accordingly, the silane treatment agent contains a silane compound capable of reacting with surface atoms of the particulate oxide, thereby forming a covalent bond between the surface atoms of the particulate mixed oxide and the silane compound. Additionally, the silane compound may contain one or more polymerizable double bonds reactive in a crosslinking reaction after the particulate dental filler is incorporated in a polymerizable dental restorative composition. The silane treatment agent may contain one or more silane compounds. Preferably, the silane compound provides a polymerizable ligand capable of crosslinking which may be a compound of one of the following formulae (I), (II) and (III), or a hydrolysis product thereof

$$X_rR_{3-r}SiL \qquad (I)$$

$$X_rR_{2-r}SiL'L'' \qquad (II)$$

$$X_rSiL'L''L''' \qquad (III)$$

wherein
X represents a hydrolyzable group;
R represents an alkyl, cycloalky, cycloalkylalkyl, aralkyl or aryl group,
L, L', L", and L'"
 which may be the same or different represent independent from each other an organic group containing one or more polymerizable double bonds;
r is an integer of 1 to 3,
whereby the sum of X, R, L, L', L", and L'" is 4 for each of formula (I), (II), and (III).

Preferably, X is a halogen atom or OR¹, wherein R¹ is an alkyl, cycloalky, cycloalkylalkyl, aralkyl or aryl group. More preferably, R or R¹ are independently an alkyl group.

In order to impart crosslinking capability to the organo-functional silicon compound, L, L', L", and L'" contain one or more polymerizable double bonds capable of taking part in a crosslinking reaction. In a preferred embodiment, L, L', L″, and L‴ may be selected from the group of allyl, (meth)acrylic ester groups, and (meth)acrylic amide groups.

An alkyl group may be straight-chain or branched C1-16 alkyl group, typically a C1-8 alkyl group. Examples for a C1-6 alkyl group can include linear or branched alkyl groups having 1 to 6 carbon atoms, preferably 1 to 4 carbon atoms, for example, methyl, ethyl, n-propyl, isopropyl, n-butyl, isobutyl, sec-butyl, tert-butyl, n-pentyl, isopentyl and n-hexyl. A cycloalkyl group may be a C3-16 cycloalkyl group. Examples of the cycloalkyl group can include those having 3 to 14 carbon atoms, for example, cyclopropyl, cyclobutyl, cyclopentyl and cyclohexyl. A cycloalkylalkyl group can include those having 4 to 22 carbon atoms. Examples for a cycloalkylalkyl group can include a combination of a linear or branched alkyl group having 1 to 6 carbon atoms and a cycloalkyl group having 3 to 14 carbon atoms. Examples of the cycloalkylalkyl group can for example, include methylcyclopropyl, methylcyclobutyl, methylcyclopentyl, methylcyclohexyl, ethylcyclopropyl, ethylcyclobutyl, ethylcyclopentyl, ethylcyclohexyl, propyl-cyclopropyl, propylcyclobutyl, propylcyclopentyl, propyl-cyclohexyl. An aralkyl group may be a C7-26 aralkyl group, typically a combination of a linear or branched alkyl group having 1 to 6 carbon atoms and an aryl group having 6 to 10 carbon atoms. Specific examples of an aralkyl group are a benzyl group or a phenylethyl group. An aryl group can include aryl groups having 6 to 10 carbon atoms. Examples of the aryl group are phenyl and naphtyl.

The C1-6 alkyl group and the C3-14 cycloalkyl group may optionally be substituted by one or more members of the group selected from a C1-4 alkyl group, C1-4 alkoxy group, a phenyl group, and a hydroxy group. Examples for a C1-4 alkyl group can include linear or branched alkyl groups having 1 to 4 carbon atoms, for example, methyl, ethyl, n-propyl, isopropyl, n-butyl, isobutyl, sec-butyl, tert-butyl. Examples for an C1-4 alkoxy group can include linear or branched alkoxy groups having 1 to 4 carbon atoms, for example, methoxy, ethoxy, n-propoxy, isopropoxy, n-butoxy, isobutoxy, sec-butoxy, and tert-butoxy.

Aryl groups may contain 1 to 3 substituents. Examples of such substituents can include halogen atoms, C1-4 alkyl groups, C1-4 alkoxy groups, C1-4 alkylthio groups, C1-4 alkylsulfonyl groups, carboxyl group, C2-5 alkoxycarbonyl groups, and C1-4 alkylamino groups. Here, illustrative of the halogen atoms can be fluorine, chlorine, bromine and iodine. The C1-4 alkyl groups are, for example, methyl, ethyl, n-propyl, isopropyl and n butyl. Illustrative of the C1-4 alkoxy groups are, for example, methoxy, ethoxy and propoxy. Illustrative of the C1-4 alkylthio groups are, for example, methylthio, ethylthio and propylthio. Illustrative of the C1-4 alkylsulfonyl groups are, for example, methylsul-fonyl, ethylsulfonyl and propylsulfonyl. Illustrative of the C2-5 alkoxycarbonyl groups can be those having alkoxy groups each of which contains 1 to 4 carbon atoms, for example, methoxycarbonyl, ethoxy carbonyl and propoxy-carbonyl. Illustrative of the C1-8 alkylamino groups can be those having one or two alkyl groups each of which contains 1 to 4 carbon atoms, for example, methylamino, dimethyl-amino, ethyl amino and propylamino. The alkyl moieties in these substituents may be linear, branched or cyclic.

Preferably, the particles of the particulate dental filler of the present invention have a porosity of at most 30 percent, preferably at most 25 percent, and still more preferred at most 20 percent, as measured by the mercury method in accordance with DIN 66 133.

Preferably, the particulate dental filler composition of the present invention has a BET surface of at most 20 m$^2$/g, more preferably of at most 20 m$^2$/g, still more preferably of at most 5 m$^2$/g as determined by DIN ISO 9277:2003-05 Bestimmung der spezifischen Oberfläche von Feststoffen durch Gasadsorption nach dem BET-Verfahren (ISO 9277: 1995). In case the BET surface is greater than 20 m$^2$/g, the bulk density of the particulate dental filler composition tends to be too low so that the particulate filler cannot be incorporated into a dental composition without excessively increasing the viscosity of the dental composition.

The particles of the particulate dental filler of the present invention have a median particle size (D50) of from 1 to 5000 nm, preferably, 10 to 1000 nm. The median particle size (D50) is measured after any aggregates of the composite filler particles have been broken up and dispersed, for example, by sonication for about 10 minutes in a suitable dispersion medium.

The particulate dental filler obtained by the process of the present invention comprises generally spherical primary filler particles. The primary particles need not be truly spherical, but should at least be rounded to the extent that a fluid-like movement of the particles is not substantially impeded. The spherical shape of the generally spherical primary particles is the result of the thermal treatment in the pulsed reactor according to the present invention and does not require an additional milling step.

The particulate dental filler obtained by the process of the present invention comprises generally amorphous primary filler particles. The primary particles may contain crystalline domains. However, the content of crystalline domains in the primary particles is preferably less that 50 percent by volume, more preferably 30 percent by volume. The amorphous morphology of the primary particles provides good transparency, gloss, and opalescence in a dental composition.

Moreover, the particulate dental filler obtained by the process of the present invention comprises primary filler particles having a refractive index of from 1.4 to 1.6, preferably 1.42 to 1.55. According to a first specific preferred embodiment, the refractive index of the primary filler particles is in the range of from 1.43 to 1.50. According to a second specific preferred embodiment, the refractive index of the primary filler particles is in the range of from 1.51 to 1.53.

According to a preferred embodiment, the mixed oxide contains tungsten, ytterbium, and/or bismuth.

The particulate dental filler of the present invention may be used for the preparation of a dental composition. A dental composition is preferably a dental restorative material. Specifically, the present invention provides a dental restorative material comprising
(i) the particulate dental filler composition according to the present invention;
(ii) one or more polymerizable compounds and/or one or more polymers; and optionally
(iii) a polymerization initiator system.

According to a preferred embodiment, the dental composition contains a dental filler composition obtainable according to the process of the present invention, wherein the mixed oxide contains tungsten, ytterbium, and/or bismuth.

The dental restorative material may be selected from a dental composite, a dental cement or a resin reinforced dental cement. A dental composite may be a highly filled dental composite, a flowable composite, a compomer, a root canal sealer, or a pit and fissure sealant. A dental cement may be a glass ionomer cement or a luting cement.

In case the restorative material contains one or more polymers, the polymers may contain polymerizable groups and represent a polymerizable polymer. Preferably, the polymerizable polymer has a molecular weight of at least 10,000 Da, more preferably at least 1500 Da, and still more preferably, 20000 Da.

In case the dental restorative material contains a polymerizable compound, the polymerizable compound is preferable a compound having at least one polymerizable group. Generally in dental compositions, radical polymerization is performed. Therefore, the polymerizable group is typically a radical polymerizable group. As the polymerizable group, (meth)acrylolylamino or a (meth)acryloyloxy group, is preferable. are selected from acrylates and methacrylates such as methyl acrylate, methyl methacrylate, ethyl acrylate, ethyl methacrylate, propyl acrylate, propyl methacrylate, isopropyl acrylate, isopropyl methacrylate, benzyl (meth)acrylate, lauryl (meth)acrylate, 2-hydroxyethyl acrylate, 2-hydroxyethyl methacrylate (HEMA), hydroxypropyl acrylate, hydroxypropyl methacrylate, tetrahydrofurfuryl acrylate, tetrahydrofurfuryl methacrylate, glycidyl acrylate, glycidyl methacrylate, the diglycidyl methacrylate of bis-phenol A ("bis-GMA"), glycerol mono- and di-acrylate, glycerol mono- and di-methacrylate, ethyleneglycol diacrylate, ethyleneglycol dimethacrylate, polyethyleneglycol diacrylate (where the number of repeating ethylene oxide units vary from 2 to 30), polyethyleneglycol dimethacrylate (where the number of repeating ethylene oxide units vary from 2 to 30 especially triethylene glycol dimethacrylate ("TEGDMA"), neopentyl glycol diacrylate, neopentylglycol dimethacrylate, trimethylolpropane triacrylate, trimethylol propane trimethacrylate, mono-, di-, tri-, and tetra- acrylates and methacrylates of pentaerythritol and dipentaerythritol, 1,3-butanediol diacrylate, 1,3-butanediol dimethacrylate, 1,4-butanedioldiacrylate, 1,4-butanediol dimethacrylate, 1,6-hexane diol diacrylate, 1,6-hexanediol di(meth)acrylate, di-2-methacryloyloxethyl hexamethylene dicarbamate, di-2-methacryloyloxyethyl trimethylhexanethylene dicarbamate, di-2-methacryloyl oxyethyl dimethylbenzene dicarbamate, methylene-bis-2-methacryloxyethyl-4-cyclohexyl carbamate, di-2-methacryloxyethyl-dimethylcyclohexane dicarbamate, methylene-bis-2-methacryloxyethyl-4-cyclohexyl carbamate, di-1-methyl-2-methacryloxyethyl-trimethylhexamethylene dicarbamate, di-1-methyl-2-methacryloxyethyl-dimethylbenzene dicarbamate, di-1-methyl-2-methacryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-2-methacryloxyethyl-4-cyclohexyl carbamate, di-1-methyl-2-methacryloxyethyl-hexamethylene dicarbamate, di-1-methyl-2-methacryloxyethyl-trimethylhexamethylene dicarbamate, di-1-methyl-2-methacryloxyethyl-dimethylbenzene dicarbamate, di-1-methyl-2-metha-cryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-1-chloromethyl-2-methacryloxyethyl4-cyclohexyl carbamate, 2,2'-bis(4-methacryloxyphenyl)propane, 2,2'bis(4-acryloxyphenyl)propane, 2,2'-bis[4(2-hydroxy-3-methacryloxy-phenyl)]propane, 2,2'-bis[4 (2-hydroxy-3-acryloxy-phenyl)propane, 2,2'-bis(4-methacryloxyethoxyphenyl)propane, 2,2'-bis(4-acryloxyethoxyphenyl)propane, 2,2'-bis(4-methacryloxypropoxyphenyl)propane, 2,2'-bis(4-acryloxypropoxyphenyl)propane, 2,2'-bis(4-methacryloxydiethoxyphenyl)propane, 2,2'-bis(4-acryloxydiethoxyphenyl)propane, 2,2'-bis[3(4-phenoxy)-2-hydroxypropane-1-methacrylate]propane, and 2,2'-bis[3(4-phenoxy)-2-hydroxypropane-1-acryalte]propane, 2-(N,N-dimethylamino)ethyl (meth)acrylate, 2,3-dibromopropyl (meth)acrylate, 2-hydroxyethyl (meth)acrylate, 6-hydroxyhexyl (meth)acrylate, 10-hydroxydecyl (meth)acrylate, propylene glycol mono(meth)acrylate, glycerol mono(meth)acrylate, erythritol mono(meth)acrylate, N-methylol (meth)acrylamide, N-hydroxyethyl (meth)acrylamide, N-(dihydroxyethyl)(meth)acrylamide, (meth)acryloyloxy-dodecylpyridinium bromide, (meth)acryloyloxydodecylpyridinium chloride, (meth)acryloyloxyhexadeylpyridinium chloride, (meth)acryloyloxydecylammonium chloride, ethylene glycol di(meth)acrylate, triethylene glycol di(meth)acrylate, propylene glycol di(meth)acrylate, neopentyl glycol di(meth)acylate, 1,6-hexanediol di(meth)acrylate, 1,10-decanediol di(meth)acrylate, bisphenol A diglycidyl (meth)acrylate, 2,2-bis[4-(meth)acryloyloxyethoxyphenyl]propane, 2,2-bis[4-(meth)acryloyloxyolyothoxyphenyl]propane, 2,2-bis[4-[3-((meth)acryloyloxy-2-hydroxypropoxy]phenyl]propane, 1,2-bis[3-(meth)acryloyloxy-2-hydroxypropoxylethane, pentaerythritol di(meth)acrylate, [2,2,4-trimethylhexamethylenebis(2-carbamoyloxyethyl)]dimethacrylate (commonly known as "UDMA trimethylolpropane tri(meth)acrylate, trimethylolethane tri(meth)acrylate, tetramethylolmethane tri(meth)acrylate, pentaerythritol tetra(meth)acrylate, dipentaerythritol hexa(meth)acrylate, N,N'-(2,2,4-trimethylhexamethylene)bis[2-(aminocarbonyloxy) propane-1,3-diol] tetramethacrylate, and 1,7-diacryloyloxy-2,2,6,6-tetraacryloyloxymethyl-4-oxyheptane. Other suitable examples of polymerizable compounds are isopropenyl oxazoline, vinyl azalactone, vinyl pyrrolidone, styrene, divinylbenzene, urethane acrylates or methacrylates, epoxy acrylates or methacrylates and polyol acrylates or methacrylates. Preferably, the polymerizable compound has a molecular weight of at most 10,000 Da, more preferably at most 8000 Da, and still more preferably, 5000 Da.

In case the dental composition is a radically polymerizable composition, then the dental composition preferably contains a polymerization initiator system. The type of the polymerization initiator is not particularly limited and can be selected from polymerization initiators commonly used in the dental field. The initiator system may be a photoinitiator system or a chemical initiator system. Particularly, photopolymerization initiators and chemical polymerization initiators may be used alone, or two or more of them may be used in combination.

Examples of suitable photopolymerization initiators include alpha-diketones or (bis)acylphosphine oxides. Examples of the alpha-diketones used as the photopolymerization initiator include camphorquinone, 9,10-phenanthrenequinone, 2,3-pentadione, 2,3-octadione, 4,4'-oxybenzyl, and acenaphthenequinone. Camphorquinone having the maximum absorption wavelength in the visible light range is preferred. Examples of the acylphosphine oxides include 2,4,6-trimethylbenzoylmethoxyphenylphosphine oxide, 2,4,6-trimethylbenzoyldiphenylphosphine oxide, 2,6-dimethoxybenzoyldiphenylphosphine oxide, 2,6-dichlorobenzoyldiphenylphosphine oxide, 2,4,6-trimethylbenzoylethoxyphenylphosphine oxide, 2,3,5,6- tetramethylbenzoyldiphenylphosphine oxide, and benzoyl di-(2,6-dimethylphenyl)phosphonate. Examples of the bisacylphosphine oxides include bis-(2,6-dichlorobenzoyl)phenylphosphine oxide, bis-(2,6-dichlorobenzoyl)-2,5-dimethylphenylphosphine oxide, bis-(2,6-dichlorobenzoyl)-4-propylphenylphosphine oxide, bis-(2,6-dichlorobenzoyl)-1-naphthylphosphine oxide, bis-(2,6-dimethoxybenzoyl)phenylphosphine oxide, bis-(2,6-dimethoxybenzoyl)-2,4,4-trimethylpentylphosphine oxide, bis-(2,6-dimethoxybenzoyl)-2,5-dimethylphenylphosphine oxide, bis-(2,4,6-trimethylbenzoyl)phenylphosphine oxide, and (2,5,6-trimethylbenzoyl)-2,4,4-trimethylpentylphosphine oxide.

A chemical polymerization initiator may be an organic peroxide selected from ketone peroxide, hydroperoxide, diacyl peroxide, dialkyl peroxide, peroxyketal, peroxyester, and peroxydicarbonate. A ketone peroxide may be selected from methyl ethyl ketone peroxide, methyl isobutyl ketone peroxide, methylcyclohexanone peroxide, and cyclohexanone peroxide. A hydroperoxide may selected from 2,5-dimethylhexane-2,5-dihydroperoxide, diisopropylbenzene hydroperoxide, cumene hydroperoxide, and t-butyl hydroperoxide. A diacyl peroxide may be selected from acetyl peroxide, isobutyryl peroxide, benzoyl peroxide, decanoyl peroxide, 3,5,5-trimethylhexanoyl peroxide, 2,4-dichlorobenzoyl peroxide, and lauroyl peroxide. A dialkyl peroxide may be selected from di-t-butyl peroxide, dicumyl peroxide, t-butyleumyl peroxide, 2,5-dimethyl-2,5-di(t-butylperoxy)hexane, 1,3-bis(t-butylperoxyisopropyl)benzene, and 2,5-dimethyl-2,5-di(t-butylperoxy)-3-hexyne. A peroxyketal may be selected from 1,1-bis(t-butylperoxy)-3,3,5-trimethylcyclohexane, 1,1-bis(t-butylperoxy)cyclohexane, 2,2-bis(t-butylperoxy)butane, 2,2-bis(t-butylperoxy)octane, and 4,4-bis(t-butylperoxy)valeric acid-n-butyl ester. A peroxyester may be selected form t-butvlperoxy acetate, t-butylperoxy-2-ethyl hexanoate, alpha-cumyl peroxyneodecanoate, t-butyl peroxyneodecanoate, t-butyl peroxypivarate, 2,2,4-trimethylpentylperoxy-2-ethyl hexanoate, t-amylperoxy-2-ethyl hexanoate, di-t-butylperoxy isophthalate, di-t-butylperoxy hexahydroterephthalate, t-butylperoxy-3,3,5-trimethyl hexanoate, t-butylperoxy benzoate, and t-butylperoxymaleic acid. A peroxydicarbonate maybe selected from di-3-methoxy peroxydicarbonate, di-2-ethylhexyl peroxydicarbonate, bis(4-t-butyleyelohexyl)peroxydicarbonate, diisopropyl peroxydicarbonate, di-n-propyl peroxydicarbonate, di-2-ethoxyethyl peroxydicarbonate, and diallyl peroxydicarbonate.

The amount of the polymerization initiator to be added in the present invention is not particularly limited. Preferably, 0.01 to 10 parts by weight of the polymerization initiator per 100 parts by weight of the polymerizable composition may be used. When the amount of the polymerization initiator is less than 0.01 part by weight, polymerization may not proceed sufficiently and thereby mechanical strength may be reduced. Therefore, the amount is more preferably at least 0.1 part by weight. On the other hand, when the amount of the polymerization initiator exceeds 10 parts by weight, in the case where the polymerization initiator itself has low polymerization performance, sufficient mechanical strength may not be obtained and furthermore precipitation from the composition may occur.

The dental composition of the present invention may further contain a polymerization accelerator. Examples of the polymerization accelerator are amines and sulfinic acids and salts thereof. Amines may be aliphatic amines or aromatic amines. Examples of aliphatic amines include primary aliphatic amines such as n-butylamine, secondary aliphatic amines such as diisopropylamine, and tertiary aliphatic amines such as N-methyldiethanolamine, N-ethyldiethanolamine, N-n-butyldiethanolamine, N-lauryldiethanolamine, 2-(dimethylamino)ethyl methacrylate, N-methyldiethanolamine dimethacrylate, N-ethyldiethanolamine dimethacrylate, triethanolamine monomethacrylate, triethanolamine dimethacrylate, triethanolamine trimethacrylate, triethanolamine, trimethylamine, triethylamine, and tributylamine, tertiary aliphatic amines are preferred. Aromatic amines may be selected from N,N-di(2-hydroxyethyl)-p-toluidine, 4-N,N-dimethylaminobenzoic acid ethyl ester, N,N-dimethylaminobenzoic acid n-butoxyethyl ester, and 4-N,N-dimethylaminobenzophenone. A sulfinic acid or salt thereof may be selected from sodium benzenesulfinate, sodium p-toluenesulfinate, and sodium 2,4,6-triisopropyl-benzenesulfinate.

The amount of polymerization accelerator is not particularly limited. The amount may be selected from the range of from 0.001 to 5 parts by weight of polymerization accelerator per 100 parts by weight of the polymerizable composition.

The dental composition of the present invention may further contain a polymerization inhibitor. The inhibitor may be any conventionally known inhibitor which does not interfere with the desired reaction. The inhibitor may be selected from 2,6-di-tert-butyl-p-cresol (BHT), hydroquinone, hydroquinone monomethyl ether, tert.-butyl hydrochinone (TBHQ), TEMPO, and phenothiazin.

In case the dental composition is not a radically polymerizable composition, such as a dental cement composition, then an initiator system is not required. Accordingly, a dental composition may be a dental cement comprising
  (i) the particulate dental filler composition according to the present invention, and
  (ii) one or more polyacidic polymers.

A dental cement is usually powder liquid systems consisting of linear poly(alkenoic acid)s as polyacidic polymers and reactive ion releasing active glasses. The most common poly(alkenoic acid)s are polymers such as polyacrylic acid or copolymers of acrylic and itaconic acid, acrylic acid and maleic acid and to some degree a copolymer of acrylic acid with methacrylic acid. Preferably, a polyacidic polymers has a molecular weight of from 10,000 to 200,000 Da, more preferably 15,000 to 120,000 Da. In the presence of water, the poly(alkenoic acid) attacks the glass powder whereby metal ions such as calcium, aluminum and strontium are released under formation of intra- and intermolecular salt bridges which crosslink the composition. The particulate dental filler composition of the present invention may be incorporated into dental cement either as an unreactive glass filler or as a reactive glass filler.

A dental cement containing the particulate dental filler composition according to the present invention may further contain an additional filler. The additional filler includes glass particles such as barium aluminum-borosilicate glass, barium aluminofluorosilicate glass and mixtures thereof. In these materials, barium can also be substituted by strontium, and may also contain fluoride.

The dental composition of the present invention may further contain a pH adjuster, an ultraviolet absorber, an antioxidant, a colorant, an antimicrobial agent, a thickening agent, a fluorine ion sustained-releasable filler and/or a fluorescent agent. A fluorine ion sustained-releasable filler may be selected from sodium fluoride, calcium fluoride, fluoroaluminosilicate glass, or sodium monofluorophosphate. An antimicrobial agent may be a surfactant having an antibacterial activity, such as 12-(meth)acryloyloxydodecylpyridinium bromide or cetylpyridinium chloride.

According to the present invention, a process for the preparation of a dental restorative material comprises a step of incorporating the dental filler composition into a dental resin matrix. The resin matrix may contain polymerizable compounds and/or polyacidic polymers.

In case of a particulate dental filler for use in a dental cement, the polymerizable compound may also be a modified polyacid having polymerizable double bonds. It is possible to use a combination of both types of polymerisations for providing a resin reinforced dental cement.

The additional filler includes glass particles such as barium aluminum-borosilicate glass, barium aluminofluorosilicate glass and mixtures thereof. In these materials, barium can also be substituted by strontium, and may also contain fluoride. Other useful materials include calcium hydroxy ceramics, and others such as those fillers disclosed in EP2604247 or U.S. Pat. Nos. 5,338,773, 5,710,194, 4,758,612, 5,079,277, and 4,814,362. These materials may have any morphology or shape, including spheres, regular or irregular shapes, filaments or whiskers, and the like and silane treated (silane coupled) or provided with other treatments as is conventional for dental fillers.

EXAMPLES

The present invention will now be explained in further detail with reference to the following examples.

Example 1

Preparation of Particulate Dental Filler Composition A:

A mixture may be prepared by weighing 100.0 g NALCO 1034a silica sol, adding 3.15 g 70 wt % $HNO_3$ solution (or alternatively, 2.20 g methanesulfonic acid), and adding zirconium acetate, such that an oxide mixture of approximately 73 wt % silica to 27 wt % zirconia on an oxide weight basis is obtained.

The geometry of the pulsed reactor may be defined by the combustion chamber length to combustion chamber diameter ratio of 2.2 and by the resonance tube length to resonance tube diameter ratio of 33.

The mixture may be introduced into the front section of the resonance tube in the form of an aerosol. The mixture may be introduced at a rate of 10 kg/h at an inlet temperature of 850° C. The frequency may be set to 25 Hz and the pressure amplitude at the outlet of the combustion chamber may be set to be 10 mbar. Prior to separation, the particle containing gas may be cooled at temperature of about 150° C. by the introduction of air. Powder separation may be carried out by means of filters having a filter area of 24 $m^2$.

The powder may be silanated for providing a particulate dental filler composition of the present invention. The particulate dental filler composition may be used in a dental restorative composition.

Example 2

Preparation of Particulate Dental Filler Composition B:

A mixture may be prepared by weighing 1300.0 g TEOS and 460.0 g tetra-n-propyl zirconate (Tyzor® NPZ). The geometry of the pulsed reactor is as in Example 1.

The mixture may be introduced into the front section of the resonance tube in the form of an aerosol. The mixture may be introduced at a rate of 10 kg/h at an inlet temperature of 850° C. The frequency may be set to 25 Hz and the pressure amplitude at the outlet of the combustion chamber may be set to be 10 mbar. Prior to separation, the particle containing gas may be cooled at temperature of about 150° C. by the introduction of air. Powder separation may be carried out by means of filters having a filter area of 24 $m^2$.

The powder may be silanated for providing a particulate dental filler composition of the present invention. The particulate dental filler composition may be used in a dental restorative composition.

The invention claimed is:

1. Process for preparation of a particulate dental filler composition, comprising steps of:
   (a) introducing a mixture containing
      (a1) a silica precursor component, and
      (a2) a solution or dispersion of one or more compounds of aluminum, zinc, titanium, zirconium, tungsten, ytterbium, hafnium, bismuth, barium, strontium, silver, tantalum, lanthanum, tin, boron, or cerium, into a pulsed reactor;
   (b) converting the silica precursor component and the one or more compounds into a particulate mixed oxide with a pulsed gas flow resulting from flameless combustion; wherein the formation of the particulate mixed oxide is carried out in a single step in the pulse reactor;
   (c) isolating the particulate mixed oxide from the pulsed reactor;
   (d) optionally subjecting the particulate mixed oxide to a heat treatment step; and
   (e) treating the particulate mixed oxide or heat-treated particulate mixed oxide with a silane treatment agent for obtaining a particulate dental filler composition; wherein the silane treatment agent contains one or more silane compounds capable of forming a covalent bond between the surface atoms of the particulate mixed oxide and the one or more silane compounds, and the one or more silane compounds contain one or more polymerizable double bonds reactive in a crosslinking reaction after the particulate dental filler composition is incorporated in a polymerizable dental restorative composition.

2. The process according to claim 1, wherein the one or more compound contains one or more elements selected from aluminum, zinc, titanium, zirconium, tungsten, ytterbium, hafnium, barium, and strontium.

3. The process according to claim 1, wherein the step of converting the silica precursor component and the compounds into a particulate mixed oxide with a pulsed gas flow resulting from flameless combustion further comprises forming a coating on the outer surface of the particulate mixed oxide.

4. The process according to claim 3, wherein the coating contains an oxide, nitride, a carbide, a silicide, a boride or a fluoride of a metal, a metalloid and/or a lanthanoid.

5. Process for a preparation of a dental restorative material comprising steps of:
   (i) providing a dental filler composition obtained according to a process comprising steps of:
      (a) introducing a mixture containing
         (a1) a silica precursor component, and
         (a2) a solution or dispersion of one or more compounds of aluminum, zinc, titanium, zirconium, tungsten, ytterbium, hafnium, bismuth, barium, strontium, silver, tantalum, lanthanum, tin, boron, or cerium, into a pulsed reactor;
      (b) converting the silica precursor component and the one or more compounds into a particulate mixed oxide with a pulsed gas flow resulting from flameless combustion;

wherein the formation of the particulate mixed oxide is carried out in a single step in the pulse reactor;
(c) isolating the particulate mixed oxide from the pulsed reactor;
(d) optionally subjecting the particulate mixed oxide to a heat treatment step; and
(e) treating the particulate mixed oxide or heat-treated particulate mixed oxide with a silane treatment agent for obtaining a particulate dental filler composition;
wherein the silane treatment agent contains one or more silane compounds capable of forming a covalent bond between the surface atoms of the particulate mixed oxide and the one or more silane compounds, and the one or more silane compounds contain one or more polymerizable double bonds reactive in a crosslinking reaction after the particulate dental filler composition is incorporated in a polymerizable dental restorative composition;
(ii) providing one or more polymerizable compounds and/or one or more polymers; and optionally
(iii) providing a polymerization initiator system; and
(iv) incorporating the dental filler composition into a dental resin matrix.

* * * * *